United States Patent [19]

Carosio

[11] 4,119,713

[45] Oct. 10, 1978

[54] ANALGESIC AND ANTI-INFLAMMATORY COMPOSITION

[76] Inventor: Sam Carosio, 111 West St., Englewood, N.J. 07631

[21] Appl. No.: 767,140

[22] Filed: Feb. 9, 1977

[51] Int. Cl.$^2$ .................... A61K 35/12; A61K 35/56; A61K 31/355; A61K 31/05

[52] U.S. Cl. ..................................... 424/95; 424/105; 424/284; 424/346

[58] Field of Search .................. 424/95, 105, 284, 346

[56] References Cited

U.S. PATENT DOCUMENTS

| | | | |
|---|---|---|---|
| 40,668 | 11/1863 | Anderson | 424/95 |
| 43,403 | 7/1864 | Grows | 424/95 |
| 3,780,185 | 12/1973 | Fields | 424/284 |
| 3,887,702 | 6/1975 | Baldwin | 424/284 |

Primary Examiner—Stanley J. Friedman
Attorney, Agent, or Firm—Constantine A. Michalos

[57] ABSTRACT

An analgesic and anti-inflammatory composition for treating osteoarthritis, rheumatoid arthritis, and rheumatism which comprises in synergistic combination, menthol, vitamin E, fresh eggs, honey, and an alcohol solvent in an intimate admixture. A method for preparing said composition is also disclosed. One application of the composition to the afflicted area will usually provide 12 to 24 hours of complete pain relief without any side effects.

5 Claims, No Drawings

ANALGESIC AND ANTI-INFLAMMATORY COMPOSITION

BACKGROUND OF THE INVENTION

1. Field of the Invention

In general the present invention is related to theropeutic compositions for external use. More particularly, this invention is concerned with an analgesic and anti-inflammatory composition for the treatment of arthritis and rheumatism.

2. Description of Prior Art

At present, about 20 million persons in the United States are afflicted with some form of arthritis requiring medical care. The annual cost of this disease to the national economy in terms of lost wages and medical care bills has become a staggering 13 billion dollars. Although a tremendous amount of research effort has been expended in studying this disease the cause or cure of arthritis has not been forthcoming.

However, many medicinal preparations are being used today which provide some pain relief. Unfortunately, they usually have some undesirable side effects associated with them. For example, aspirin may produce indigestion and stomach pain; indomethacin causes headaches; phenylbutazone may produce stomach ulcers; and phenacetin may lead to kidney disease. Even cortisone and other steroids, which were once hailed as miracle pain relievers for arthritis, have now been found to have serious side effects when used for long periods.

In general, prior art compositions have certain limitations and deficiencies, such as: only short term pain relief, slow acting, insufficient pain relief, insufficient therapeutic action against inflammation and stiffness, or having undesirable biological side effects.

In contrast, the present invention after one application to an afflicted area will usually provide relief of pain and inflammation within 15 minutes, and this relief will last from 12 to 24 hours. Also, this invention will not produce any side effects even after long term treatment.

SUMMARY OF THE INVENTION

The invention is concerned with an analgesic and anti-inflammatory composition for the treatment of arthritis and rheumatism, and the method for manufacturing the composition. This composition is comprised of a synergistic combination of menthol, vitamin E, fresh eggs, honey, and a pharmaceutically acceptable alcohol solvent.

Advantages of this therapeutic composition include: pain relief usually begins within 10 to 15 minutes after application, long term pain relief will usually last from 12 to 24 hours after only one application for mild to moderate cases of arthritis, and no side effects will occur even after long term usage.

Accordingly, a major object of this analgisic and anti-inflammatory composition is to provide rapid relief of the symptoms of arthritis and rheumatism.

Another object is to provide a therapeutic composition giving long term pain relief and mobility to persons suffering from arthritis and rheumatism.

Still another object is to provide a low cost anti-arthritic composition having no undesirable side effects.

A further object is to provide an analgesic and anti-inflammatory composition which does not require a physician's attendance for administration.

These and other objects and features of the invention will become more apparent by reference to the following detailed description of the preferred embodiment of the invention.

DESCRIPTION OF THE PREFERRED EMBODIMENT

The present invention, which is an externally applied therapeutic composition, is not intended to be a cure for arthritis or rheumatism. However, this novel composition has presented remarkable and superior results when administered to a large number of patients.

In general, the composition of the invention is therapeutically effective for arthritis and rheumatism over the ranges specified in Table I, where percentages are by weight.

TABLE I

| | |
|---|---|
| Menthol | 0.16 – 0.26% |
| Vitamin E (per kg of total weight) | 2050 – 3450 I.U. |
| Purified Honey | 0.16 – 0.26% |
| Fresh Eggs | 36– 60% |
| Ethanol (30 – 70%) | Balance |
| | 100% |

A preferred composition in accordance with this invention is presented in Table II, where percentages are by weight.

TABLE II

| | |
|---|---|
| Menthol | 0.21% |
| Vitamin E (per kg of total weight) | 2750 I.U. |
| Purified Honey | 0.21% |
| Fresh Eggs | 48% |
| Ethanol (50%) | Balance |
| | 100% |

An important part of this invention is the method of preparing the composition, which involves a two step process. The first step (A), utilizing therapeutically acceptable ranges, requires slowly mixing the ingredients of Table III for about 10 minutes. This may be accomplished by using a blender at a relatively low speed. The percentages shown are by weight.

TABLE III

| | |
|---|---|
| Menthol | 3.9 – 6.5% |
| Vitamin E (per kg of weight of step A) | 39,000 – 65,000 I.U. |
| Purified Honey | 3.9 – 6.5% |
| Ethanol (30 – 70%) | Balance |
| | 100% |

The intimate admixture of the ingredients of step A then becomes an ingredient of a second mixture in step B. Therapeutically acceptable ranges for step B are shown in Table IV, where the ingredients are mixed at a relatively low speed for about 10 minutes. The percentages given are by weight.

TABLE IV (Step B)

| | |
|---|---|
| Composition A | 3 – 5% |
| Fresh Eggs | 36 – 60% |
| Ethanol (30 – 70%) | Balance |
| | 100% |

The preferred concentrations for manufacturing the composition of this invention utilizes the percentages given in Table V (Step A) and Table VI (Step B). The percentages shown are by weight.

TABLE V (Step A)

| Methanol | 5.2% |
|---|---|
| Vitamin E (per kg of weight of Step A) | 52,000 I.U. |
| Purified Honey | 5.2% |
| Ethanol (50%) | Balance |
| | 100% |

TABLE VI (Step B)

| Composition A | 4% |
|---|---|
| Fresh Eggs | 48% |
| Ethanol (50%) | 48% |
| | 100% |

Although ethanol is shown as the alcohol solvent other pharmaceutically acceptable alcohols may also be used, such as isopropyl alcohol.

The resulting mixture of step B is then applied to the afflicted area of the person suffering from arthritis or rheumatism. The amount of dosage will vary with the character and severity of the pain source. Other factors affecting dosage for a particular patient are: age, sex, body weight, and general health.

In general, the application of the composition to the afflicted area will eliminate pain within 15 minutes for mild to moderate cases of arthritis. For these cases of arthritis it has been found that one application of the composition each day is adequate to eliminate pain and inflammation of the afflicted joints in the body. Therefore, the name selected for this therapeutic composition is "ALL DAY".

In severe cases of arthritis more than one application of the composition may be required each day. However, it has been found that even in these cases the effectiveness of the present invention is greater than other remedies in terms of reducing pain and inflammation without producing undesirable biological side effects.

The superior results of the present invention are shown in the case histories presented below.

EXAMPLE 1

A 48 year old male suffering from arthritis in the interphalangeal joints of both hands for the 5 previous years was treated with the composition having the preferred concentrations. After 15 minutes the pain completely disappeared and flexibility returned to his hands. Thereafter, one treatment each day eliminated the arthritic pain and restored hand flexibility. Previously, he had used aspirin, methyl solicylate compounds, and heating pads which were not as effective as the present invention in eliminating pain and inflammation in his hand.

EXAMPLE 2

A 73 year old female had been afflicted with arthritic pain in the joints of both arms and legs. The disease had been in progress for the past 20 years with increasing pain and swelling of the joints. She had been given cortisone injections but because of the undesirable side effects, this type of treatment was used only occasionally. Other types of treatment were also given which offered only short term pain relief. However, when the preferred concentrations of the present invention was applied to the afflicted areas she experienced dramatic pain relief which lasted up to 12 hours after one application. Thereafter, she was given two treatments each day using the preferred composition. She was then able to do simple housework, and some degree of flexibility returned in all of the afflicted joints.

Other case histories showed similar improvements and demonstrated the effectiveness of the present invention in eliminating pain and inflammation of arthritic joints without any side effects.

Although the biological mechanism of the present invention for combatting arthritic inflammation is not presently understood, it is believed that the synergistic combination of the ingredients of the composition produces a substance that is absorbed through the skin and effectively neutralized the inflammatory agent or mechanism of the afflicted joint.

In order to produce a time delay effect or prolonged action of the composition upon an afflicted area, a suitable excipient may be employed. For example, an effective amount of the composition may be combined with a suitable carrier base to produce either a cream, lotion, jelly, or ointment combination.

The invention has been described with particular reference to certain preferred embodiments thereof, but it will be understood that variations and modifications can be effected within the spirit and scope of the invention as described above and as defined in the appended claims.

What is claimed is:

1. An analgesic and anti-inflammatory composition for external application comprising in synergistic combination by weight:
   from about 0.16 to about 0.26 percent of menthol;
   from about 36 to about 60 percent of whole eggs;
   a concentration of vitamin E from about 2050 to about 3450 international units per kilogram of total composition weight;
   from about 0.16 to about 0.26 percent of substantially purified honey; and
   a pharmacentically acceptable diluted alcohol solvent to make 100 percent.

2. A composition as defined in claim 1 wherein said combination comprises by weight:
   from about 0.18 to about 0.24 percent of menthol;
   from about 42 to 54 percent of whole eggs;
   a concentration of vitamin E from about 2400 to about 3100 international units per kilogram of total composition weight;
   from about 0.18 to about 0.24 percent of substantially purified honey; and
   a pharmacentically acceptable diluted alcohol solvent to make 100 percent.

3. A composition as defined in claim 2 wherein said solvent is a mixture of from about 30 to about 70 percent by weight of a lower alcohol selected from a group consisting of ethanol and isopropyl alcohol, and the balance substantially water.

4. An effective amount of the composition defined in claim 1 combined with a carrier base selected from the group consisting of ointment basis, lotion bases, jelly bases, and cream bases.

5. A method for preparing an analgesic and anti-inflammatory composition as claimed in claim 1 wherein said method comprises the two successive steps of:
   (I) admixing
       (A) from about 3.9 to about 6.5 percent by weight of menthol;

(B) a concentration of vitamin E from about 39,000 to about 65,000 international units per kilogram of total weight in step (I)
(C) from about 3.9 to about 6.5 percent by weight of substantially purified honey; and
(D) a pharmaceutically acceptable diluted alcohol to make 100 percent by weight, the percentages by weight of the components in step (I); and
(II) admixing (A) from about 3.0 percent to about 5.0 percent by weight of the mixture obtained from step (I);
(B) from about 3.6 to about 6.0 percent by weight of whole eggs; and
(C) a pharmaceutically acceptable diluted alcohol solvent to make 100 percent by weight, the percentages by weight being based upon the total weight of the components in step (II).

* * * * *